(12) United States Patent
Takuno

(10) Patent No.: US 6,507,631 B1
(45) Date of Patent: Jan. 14, 2003

(54) X-RAY THREE-DIMENSIONAL IMAGING METHOD AND APPARATUS

(76) Inventor: Tetsuo Takuno, 494-46, Kuratomi, Okayama-shi, Okayama (JP)

( * ) Notice: Subject to any disclaimer, the term of this patent is extended or adjusted under 35 U.S.C. 154(b) by 0 days.

(21) Appl. No.: 09/746,599

(22) Filed: Dec. 21, 2000

(30) Foreign Application Priority Data

Dec. 22, 1999 (JP) .......................................... 11-364238

(51) Int. Cl.⁷ ................................................ H05G 1/60
(52) U.S. Cl. .......................................... 378/4; 378/22
(58) Field of Search .............................. 378/22, 4, 23, 378/24, 25

(56) References Cited

U.S. PATENT DOCUMENTS

| | | | | |
|---|---|---|---|---|
| 4,577,222 A | * | 3/1986 | Kruger et al. ............... | 358/111 |
| 4,686,692 A | * | 8/1987 | DeMeester et al. ............ | 378/4 |
| 6,256,370 B1 | * | 7/2001 | Yavuz ........................ | 378/22 |
| 6,292,530 B1 | * | 9/2001 | Yavus et al. .................. | 378/22 |

* cited by examiner

*Primary Examiner*—David P. Porta
*Assistant Examiner*—Elizabeth Gemmell
(74) *Attorney, Agent, or Firm*—Koda & Androlia

(57) ABSTRACT

An X-ray three-dimensional imaging method in which the step of irradiating an object of imaging with X-rays from an X-ray tube so as to obtain a radioactivity density as an X-ray original image is performed with at least positions of X-ray irradiation changed, thus obtaining X-ray original images at respective X-ray irradiation positions; and the step of performing irradiation from an X-ray irradiation position in a specified position with respect to a certain observation point in the object is performed, so that an X-ray transmissivity obtained by dividing planar density of radioactivity of X-rays passing through an observation point by planar density of radioactivity if it is assumed that no object of imaging is present is obtained from pixels determined from positions of the irradiation position and observation point within the X-ray original image that corresponds to the irradiation position.

17 Claims, 13 Drawing Sheets

MOVEMENT PATH OF X-RAY TUBE

IMAGE OF POINT P (to be continued)

X-RAY THREE-DIMENSIONAL IMAGING METHOD AND APPARATUS

BACKGROUND OF THE INVENTION

1. Field of the Invention

The main technical field of the present invention is the medical field, and the present invention relates to an x-ray three-dimensional imaging method and apparatus.

2. Prior Art

Diagnosis by means of X-ray photographs is indispensable in modem medicine. In particular, X-ray tomography (hereafter referred to as "X-ray CT") provides information that is extremely useful for the diagnosis of pathological changes, etc. that occur inside the cranium and in the abdomen. In addition, such tomography is used in various other applications, e.g., as one method of so-called non-destructive examination used to investigate the internal structure of cultural materials without destroying such materials.

In a conventional X-ray CT apparatus, imaging is performed by causing an X-ray tube to rotate along the ring of an X-ray detector arranged in an annular (one-dimensional) configuration. Accordingly, the X-ray detector can only obtain information for a specified section (sectional plane) of the human body constituting the object of imaging. As a result, the image that is obtained is a simple planar image, and is not suitable for obtaining a three-dimensional understanding of the structure of the object of imaging.

For example, in cases where it is desired to obtain an overall image of a certain organ, respective sectional images are obtained by setting sectional planes at several locations with respect to the organ; then, these sectional images are read by a reader (physician), and the structure of the organ is mentally envisioned. Accordingly, considerably skill and experience are required in order to comprehend an overall image of an organ by reading such images. On the other hand, in cases where a spiral X-ray CT developed in recent years is used, the X-ray tube moves in a spiral configuration so that a plurality of different sectional planes can be continuously imaged under the same conditions. Since these sectional images are stored as image information inside a computer, image processing such as the preparation of sectional images from any desired direction, the extraction and display of specified tissues organs only, or the preparation of views traced from any desired direction, etc. can be performed following imaging.

However, in cases where such a spiral X-ray CT device is used, considerable time is required for imaging, and drawbacks arise. Namely, the exposure of the patient to X-rays is increased, and there is an increased burden on the patient due to the fixed posture required. Furthermore, for organs whose movement cannot be voluntarily stopped by the patient, such as the heart, etc., clear images cannot be obtained.

Recently, therefore, methods for imaging a plurality of sectional images more efficiently than in the case of spiral CT have been proposed. In Japanese Patent Application 5-517284, a means for the efficient two-dimensional detection of X-rays is discussed, and a means for simultaneously obtaining a plurality of sectional images merely by causing the X-ray tube to perform a single circuit around the object of imaging is indicated. Furthermore, in Japanese Patent Application Laid-Open (Kokai) No. H 6-233757, clearer images are obtained by forming the irradiating X-rays into a parallel beam.

However, in the case of the former device, as sectional images that are vertically separated from the circling track of the X-ray tube are imaged, the angle formed by the sectional images and the X-rays becomes mathematically difficult to supplement, so that the sectional images become blurred. Though this problem does not occur in the latter device, there are many technical problems with regard to the device that generates a parallel X-ray beam, so that this system has not yet reached the stage of practical use. In any case, these methods are merely methods for the efficient imaging of a plurality of sectional images of the object of imaging. As evidence of this, a point that is common to both inventions is that the X-ray tube must move in a circuit around the object of imaging. When such a moving system is adopted for the X-ray tube, the size of the overall apparatus is increased, and the manufacturing method cost is also increased. Furthermore, installation, operation and maintenance of the apparatus also become difficult.

More specifically, since the X-ray tube and X-ray detector rotate about the human body at a high speed, the centrifugal force is proportional to the rotational radius, and increases in proportion to the square of the angular velocity. Accordingly, if these devices perform one circuit about the human body in 0.1 seconds, a centrifugal force that is close to 200 times the force of gravity is generated. In such a case, many technical problems occur that involves, among others, a strong mechanical strength is required in the parts that fasten the apparatus in place, a powerful driving device is required, and the apparatus must be absolutely free from vibration.

The present invention solves the above-described problems. More specifically, in the surveying of the X-ray transmission coefficients of an object of imaging, the present invention makes it possible to obtain a means that measures only the X-ray transmission coefficient at an arbitrary point in the object of imaging (which has a three-dimensional extension) independently of other points, with absolutely no need for setting sectional planes. Furthermore, the X-ray transmission coefficients at all points within the object of imaging, i.e., an X-ray three-dimensional image, can be imaged by a series of scans in the same manner as the single-image imaging of a conventional X-ray CT.

In addition, since it is not absolutely necessary for the X-ray tube to rotate about the human body during imaging, and since the X-ray detector can be fixed, the weight of the movable parts can be greatly reduced. Furthermore, as will be described later, the series of scans can be completed in an extremely short time by magnetically controlling the position at which the X-rays are generated. As a result, three-dimensional images that show no blurring can be obtained even in the case of organs that move involuntarily, such as the heart, etc. Accordingly, by imaging numerous three-dimensional images over time, it is possible to image the movement of the organ itself as a movie image.

SUMMARY OF THE INVENTION

In accordance with the above-described concept, the present invention provides an X-ray three-dimensional imaging method that comprises the following operations 1) through 4):

1) an operation in which a step of irradiating an object of imaging with X-rays from an X-ray tube, detecting a planar density of radioactivity of X-rays passing through the object of imaging by an X-ray detector in which very small pixels are arranged in a planar configuration, and obtaining such radioactivity density as an X-ray original image is performed with at least positions of X-ray irradiation changed, thus obtaining X-ray original images at respective X-ray irradiation positions;

2) an operation in which irradiation from an X-ray irradiation position in a specified position is performed with respect to a certain observation point in the object of imaging, and an X-ray transmissivity obtained by dividing planar density of radioactivity of the X-rays passing through the observation point by planar density of radioactivity in a case where it is assumed that no object of imaging is present is obtained from pixels determined from positions of the irradiation position and observation point within the X-ray original image corresponding to the irradiation position;

3) an operation in which the transmissivity of the X-rays passing through the observation point is determined by performing the operation 2) from all other X-ray irradiation positions, and an X-ray transmission coefficient at the observation point is obtained by subjecting transmissivity values to an averaging treatment; and 4) an operation in which the operations 2) and 3) are performed for all observation points in the object of imaging so that the X-ray transmission coefficients at respective observation points are determined, and distribution of the X-ray transmission coefficients in the object of imaging is obtained as an X-ray three-dimensional image.

Furthermore, the present invention provides an X-ray three-dimensional imaging apparatus that performs the method described above, and the X-ray three-dimensional imaging apparatus comprises at least: an X-ray tube which is capable of irradiating the object of imaging with X-rays and whose X-ray irradiation positions and direction can be quickly changed; an X-ray detector in which very small pixels that can detect the X-rays passing through the object of imaging and output a physical quantity that corresponds to a planar density of radioactivity of the X-rays are arranged in a planar configuration; a central processing unit which controls an operation of an X-ray tube and an X-ray detector, and which determines X-ray three-dimensional image by processing a detection data of the X-ray detector; and an output device which outputs a three-dimensional image determined by the central processing unit.

More specifically, in the present invention, the amount of information obtained per unit time is greatly increased by arranging the X-ray detector in a planar configuration instead of a linear configuration as in conventional systems. In a conventional X-ray CT device, the X-ray detector is arranged in a linear (one-dimensional) configuration. Accordingly, information (X-ray dosages) in a two-dimensional space (in mathematical terms) is collected in combination with information concerning the rotational angle of the X-ray tube (one-dimensional information). Consequently, the images that are obtained are also limited to sectional images as two-dimensional images. The present invention is characterized by the fact that the X-ray detector is arranged in a two-dimensional (planar) configuration, so that three-dimensional images, i.e., X-ray three-dimensional images can be constructed by expanding the measurement space to three dimensions.

Furthermore, as examples of application in conventional X-ray CT devices, there have been devices that are designed so that a plurality of sectional planes can be simultaneously imaged using a two-dimensional detector similar to that of the present invention as the X-ray detector. However, as described above, such devices are outside the scope of the present invention. The present invention differs from these devices in that the X-ray transmission coefficients at all points within the object of imaging can be independently and simultaneously confirmed.

DETAILED DESCRIPTION OF THE INVENTION

Figure 1:
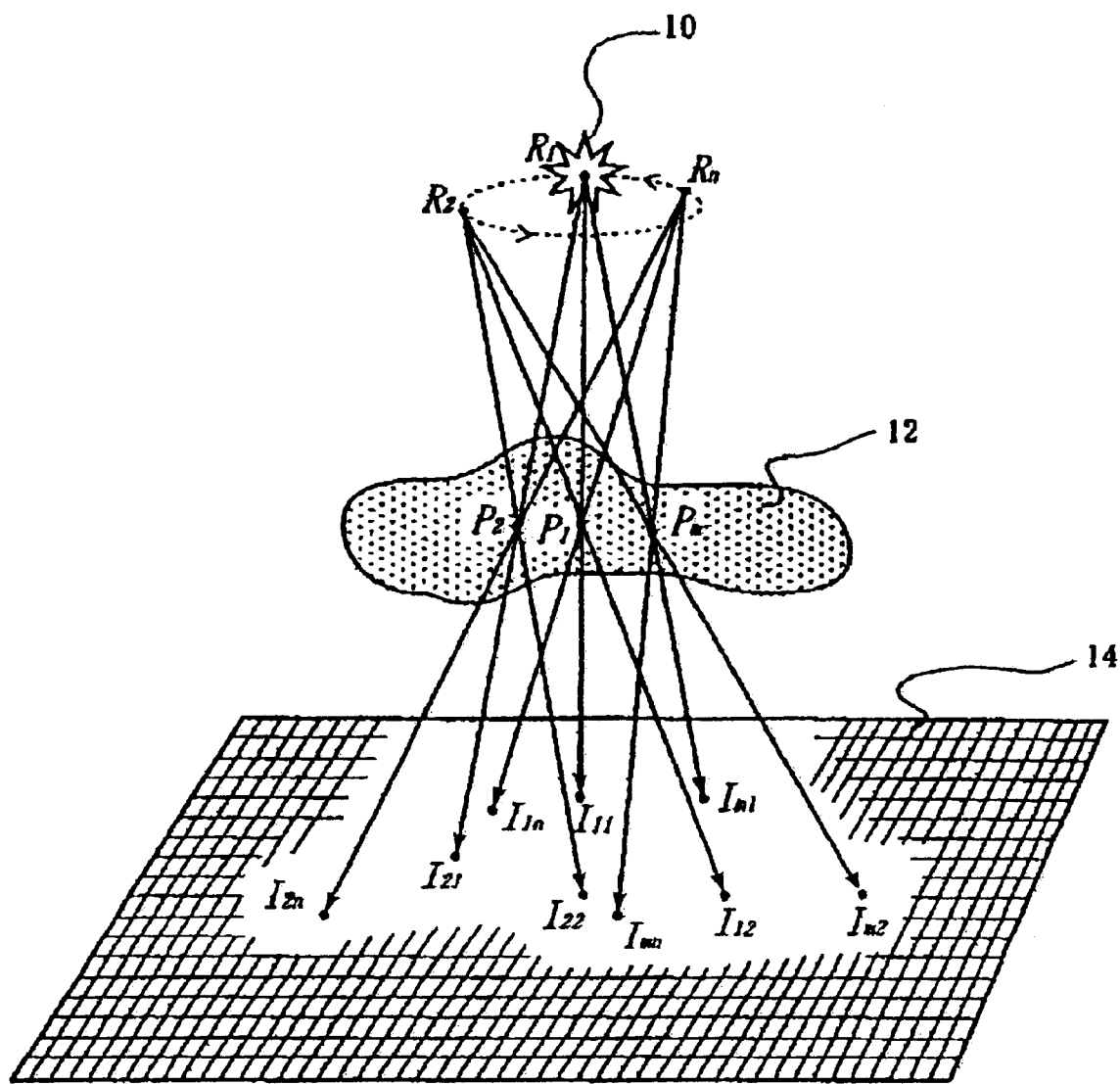
FIG. 1 is an explanatory diagram that illustrates the principle of the three-dimensional imaging device of the present invention.

An embodiment of the present invention will be described below. First, however, technical terms that are frequently used in this description will be explained.

X-ray Original Image

The distribution of the planar density of radioactivity in a certain projected plane of the X-rays passing through the object of imaging as a whole is referred to as the "X-ray original image". This includes images in which this image is recorded in some form. For example, images in which differences in the planar density of radioactivity are expressed as lighter or darker shades on a film as in a simple X-ray photograph are also referred to as X-ray original images.

X-ray Transmissivity/X-ray Transmission Coefficient

Here, it is assumed that an object of imaging that is not necessarily homogeneous, such as the human body, is sufficiently irradiated with fine linear parallel X-rays whose planar density of radioactivity is $I_0$. Then, in a case where the planar density of radioactivity of the X-rays that have passed through the object of imaging is I, the ratio $I/I_0$ is referred to as the "X-ray transmissivity". Furthermore, in a case where the object of imaging is homogeneous, the X-rays attenuate exponentially according to the distance L traveled by the X-rays through the object of imaging. Accordingly, the following expression is possible: $I=G^L \cdot I_0$. Here, G is a value that is peculiar to the material of the object of imaging. This value is designated as the X-ray transmission coefficient. In other words, the X-ray transmission coefficient refers to the proportion by which the radioactivity attenuates while the X-rays pass through a homogeneous material for a unit distance. Furthermore, even in the case of an object of imaging that is not homogeneous, such as the human body, this object can be approximated as a more or less homogeneous body if the reference is limited to a sufficiently small area that includes a certain point. Accordingly, the X-ray transmission coefficient at this point can be defined as described above.

X-ray Three-dimensional Image

In a structure such as the human body, the X-ray transmission coefficient differs according to the portion of the body that is involved. For example, the X-ray transmission coefficient of bone tissue is low, but the X-ray transmission coefficient of adipose tissue is only somewhat lower than that of water. Utilizing this fact, a physician can judge the presence or absence of pathological changes from light and dark shades in X-ray photographs on the basis of positional relationships of bones and other tissues. Assuming that the X-ray transmission coefficient can be tentatively determined at an arbitrary point P(x,y,z) in the object of imaging, the X-ray transmission coefficient at this point is a function of x,y,z, and is designated as G(x,y,z). Here, in a case where the X-ray transmission coefficients i.e., $G_1(x_1,y_1,z_1)$ through $G_n(x_n,y_n,z_n)$ for a sufficiently large number of points $P_1(x_1, y_1,z_1,)$ through $P_n(x_n,y_n,z_n)$ (which are not localized) on the same plane in the object of imaging are determined, the distribution of these X-ray transmission coefficients in a three-dimensional space is referred to as an "X-ray three-dimensional image".

In concrete terms, since an X-ray three-dimensional image consists of three-dimensional information stored in a computer, this information must be converted into an image that a human being can understand. In this conversion, it is convenient to construct a perspective view. The term "perspective view" refers to a view that is calculated as a planar image that is to be projected onto a hypothetical screen positioned opposite a hypothetical X-ray tube (installed inside a computer) after X-rays emitted from this hypothetical X-ray tube are attenuated by passing through a hypothetical object of imaging (X-ray three-dimensional image). It may be assumed that radially oriented X-rays are emitted from the hypothetical X-ray tube in this case. However, if the X-rays are assumed to be parallel X-rays, the perspective view is not enlarged or reduced according to the positional relationship of a third party. Accordingly, observation is easier in this case.

Furthermore, since X-ray transmission coefficients for respective points in the object of imaging are recorded in the computer, sectional images at specified sectional planes can also be constructed as in a conventional X-ray CT. Furthermore, since sectional planes can be taken in any desired direction, sectional planes in arbitrary directions can also be constructed. Accordingly, images of longitudinal sectional planes, which are extremely difficult to image in the case of conventional X-ray CT devices, can also be obtained. In addition, further applications are also conceivable; e.g., the course of blood vessels can be ascertained by injecting a shadow-forming agent into the blood vessels and imaging the blood vessels, and bone tissues or specified organs only can be extracted and displayed in three dimensions, etc.

Names and Functions of Instruments Used in Imaging

1. X-ray Tube

If a metal plate, etc., is heated, a thermoelectron cloud can be generated at the surface of the plate. X-rays at a wavelength near the desired wavelength can be generated by using a high voltage to accelerate this cloud to a constant velocity, and irradiating a metal known as a target with these accelerated electrons. A device which generates electrons in this way is known as a X-ray tube. The diameter of the electron beam in this case can easily be adjusted by means of a filter, etc., so that X-rays that are close to a point light source can be obtained. In recent years, furthermore, it has also become possible to control the irradiation position of X-rays at an extremely high speed by using deflection coils to change the orientation of the electron beam so that arbitrary positions on a target which has a planar extension are irradiated by the electron beam.

2. X-ray Detector

Semiconductors include sensors that are sensitive to received electromagnetic waves as physical quantities corresponding to the relative strength of the energy of the waves. In concrete terms, such sensors cause a variation in electrical resistance or generate a potential difference by the photoelectric effect or Compton effect. Accordingly, a device that picks up two-dimensional images by forming such sensors as extremely small sensors (pixels) arranged in a checkboard configuration (planar configuration) on a substrate, and respectively detecting the quantities of light received by these extremely small sensors, has been practicalized; and this device is called a solid imaging element (CCD).

In recent years, CCDs that are sensitive to X-rays, i.e., X-ray CCDs, have been developed by installing a film that blocks visible light and enhances the sensitivity to X-rays on the surface of a CCD. Such X-ray CCDs have already been used clinically to image the interior of the oral cavity, etc., in the field of dentistry. Such X-ray CCDs show a good sensitivity compared to imaging performed using X-ray fluorescent films, and also offer the advantages of good contrast and a lack of any need for developing. As a result of future technical development, it will doubtless become possible to manufacture large-size devices relatively inexpensively. The X-ray detector referred to in the present invention is such a detector in which sensors that are highly sensitive to X-rays are densely arranged in a planar configuration as in such an X-ray CCD.

3. Computer

The computer constructs an X-ray three-dimensional image of the object of imaging by controlling the position irradiated by X-rays, the irradiation dose and the irradiation time, specifying the pixels that receive X-rays passing through respective points in the object of imaging in connection with the points and the X-ray irradiation positions, and calculating the X-ray transmission coefficients at respective points in the object of imaging. Furthermore, the computer also has the function of working the X-ray three-dimensional image into a planar image that is easy to observe, such as various types of sectional images or perspective views, etc.

4. Object of Imaging

This is the object for which an X-ray three-dimensional image is to be obtained. Ordinarily, this object has a three-dimensional extension.

Method Used to Calculate X-ray Transmission Coefficients in Spatial Coordinates Methods used to construct sectional images using an X-ray CT may be divided into the principal categories of successive approximation methods and analytical methods. Currently, analytical methods constitute the mainstream of such methods. Furthermore, methods falling into the category of analytical methods include reverse projection methods, Fourier transform methods, convolution methods and filter-corrected reverse projection methods, etc. In all of these cases, analytical methods use the Radon theorem to obtain sectional images of the object of imaging. The Radon theorem states that if a fixed dose of X-rays is directed toward a certain point from any direction, and it is possible to investigate the quantity of all of the X-rays transmitted through this point, the value obtained by dividing the geometric mean of the quantity of transmitted X-rays by the irradiation dose is equal to the X-ray transmission coefficient at that point.

This Radon theorem can be applied not only to two-dimensional planes, but also to three-dimensional spaces. The present invention is characterized by the fact that the Radon theorem is extended to three dimensions. Here, a calculation method based on the reverse projection method, in which the calculations are simplest, will be described. However, it goes without saying that imaging can be similarly performed using other methods as well.

FIG. 1 illustrates the present invention. First, a sufficient number of observation points $P_1$ through $P_m$ are disposed in the object of imaging 12. The X-ray tube 10 can irradiate the object of imaging 12 by independently emitting X-rays in a conical pattern from the positions of points $R_1$ through $R_n$. Furthermore, the planar density of radioactivity per unit area immediately prior to entry into the object of imaging 12 is designated as $I_0$. The X-rays thus caused to irradiate the object of imaging 12 reach an X-ray detector surface 14 after being attenuated by the object of imaging 12, and are detected as an electrical signal. For example, among the X-rays that are emitted from point $R_j$, those X-rays that pass through point $P_i$ in the object of imaging 12 are also attenuated by other portions of the object of imaging 12, so that these X-rays reach the X-ray detector surface 14 with the dose per unit area as $I_{ij}$. Here, for the sake of simplicity, it is assumed that the area of each detection pixel on the X-ray detector surface 14 is sufficiently small, and that approximately parallel X-rays are emitted in regard to the X-ray path.

Now, noting a certain arbitrary point $P_i$ ($1 \leq i \leq m$) in the object of imaging 12, the means used to calculate the X-ray transmission coefficient $G_i$ in a sufficiently small space in the vicinity of this point will be described. The aforementioned Radon theorem can also be applied three-dimensionally. According to this theorem, $G_i$ can be approximated as follows:

$$G_i \approx (I_{i1} \cdot I_{i2} \cdot I_{i3} \cdots I_{in})^{1/n}/I_o$$

Furthermore, if $S_{ij}$ is set equal to $I_{ij}/I_o$ ($1 \leq j \leq n$), the following is obtained:

$$G_i \approx (S_{i1} \cdot S_{i1} \cdot S_{i1} \cdots S_{in})^{1/n}$$

Then, taking the logarithms of both sides, the following is obtained:

$$\ln G_i \approx 1/n \sum_{j=1}^{n} \ln S_{ij}$$

Since the X-ray transmission coefficient $G_i$ at a specified point $P_i$ in the object of imaging 12 can be determined by the above means, the three-dimensional distribution of the X-ray transmission coefficients in the object of imaging 12, i.e., an X-ray three-dimensional image, can be obtained by performing the same operation for all of the points that are to be observed in the object of imaging 12, and storing the results in respective corresponding memory cells $M_j$. It should especially be noted here that n is sufficient as the number of times of irradiation required in order to obtain an X-ray three-dimensional image. For example, in a case where the X-ray tube 10 is installed at the position of $R_j$, images of all of the observation points ($P_l$ through $P_m$) are projected onto the X-ray detector 14 as $I_{lj}$ through $I_{mj}$ as a result of X-ray irradiation from this position. Accordingly, the aforementioned $S_{lj}$ through $S_{mj}$ can be immediately determined.

As a result of the above-described operation, an X-ray three-dimensional image of the object of imaging 12 can be constructed. However, in cases where an image is constructed using this reverse projection method, the contrast is sometimes known to drop in areas where the contrast is ordinarily strong, e.g., at the boundaries between bone tissues and soft tissues, etc. In order to solve this problem, it is common to use the data obtained from the X-ray detector 14 after the data has been corrected (filter-corrected reverse projection method), or to perform further mathematical corrections for sectional planes tentatively constructed by the reverse projection method (convolution method or Fourier transform method, etc.). In the present invention as well, it goes without saying that such correction is advantageous for obtaining good images. In regard to the correction method used in this case, however, the present invention differs from cases in which corrections are performed on ordinary sectional planes in that the number of mathematical dimensions is increased by one so that it is necessary to perform a treatment on a three-dimensional space. One example of this method will be described below.

The X-ray three-dimensional image obtained as described above contains errors which causes it to differ slightly from the distribution of the X-ray transmission coefficients in the object of imaging itself. It is known that this is given by the following equation:

$$g(x,y,z)=f(x,y,z)*h(x,y,z)+n(x,y,z)$$

Here, $g(x,y,z)$ is the X-ray three-dimensional image that is obtained, $f(x,y,z)$ is the distribution of X-ray transmission coefficients (true values) in the object of imaging, $h(x,y,z)$ indicates the point image distribution function, and $n(x,y,z)$ indicates noise. Furthermore, * indicates a convolution product.

The point image distribution function refers to the image that is obtained when the object of imaging described below is observed. Here, however, the effect of noise is not considered. $f(0,0,0)=1$, $f(x,y,z)=0$; however, the origin is excluded.

Figure 2:
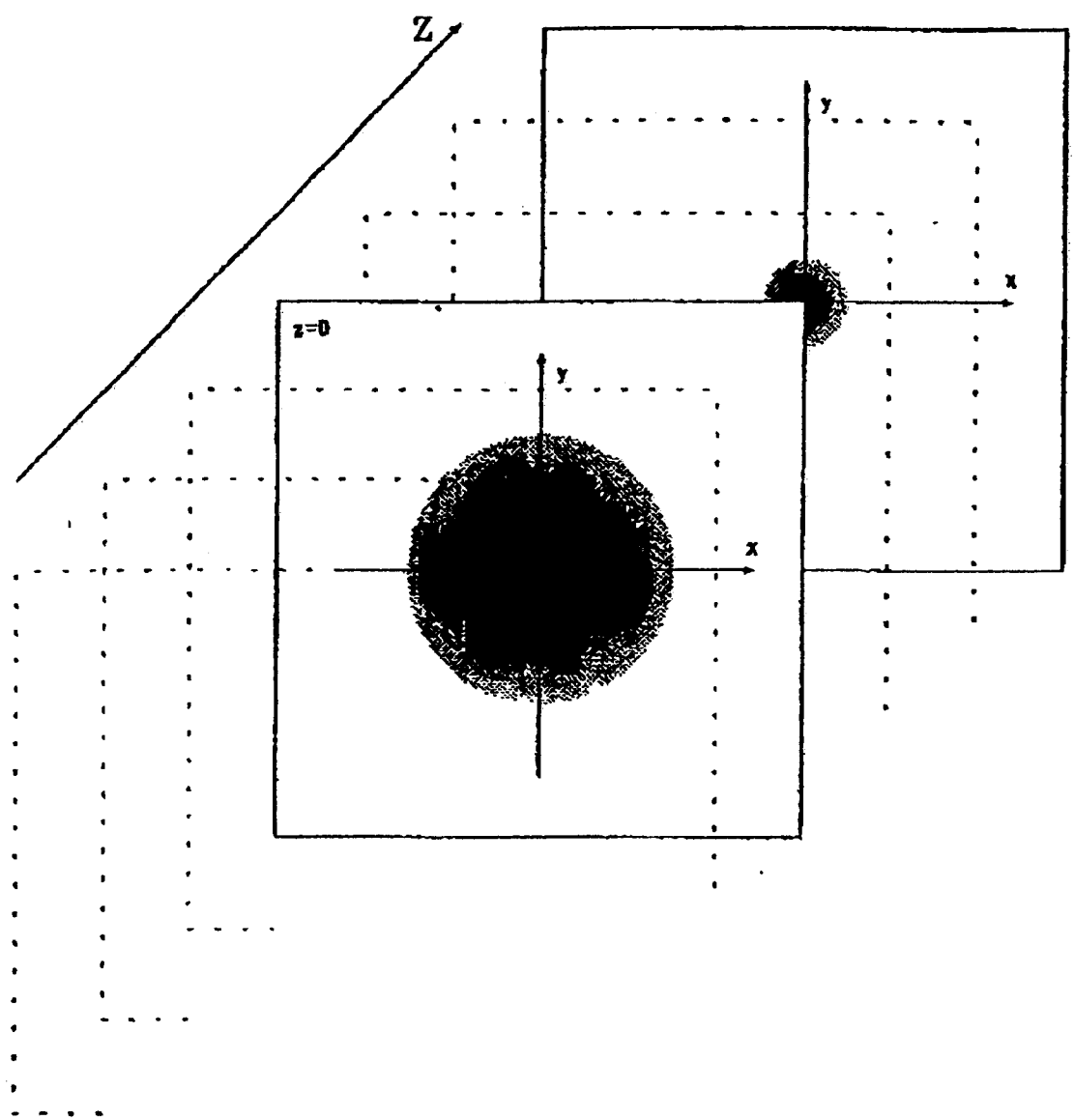
FIG. 2 is an explanatory diagram of a point image distribution function illustrating one example of the present invention.

Since some blurring occurs in an ordinary observation system, it may be predicted that an image of the type shown in FIG. 2 will be obtained when such an object of imaging is observed. This is referred to as the point image distribution function.

Now, assuming that the respective results obtained by applying a three-dimensional Fourier transform to $g(x,y,z)$, f(x,y,z), h(x,y,z) and n(x,y,z) are G(x,y,z), F(x,y,z), H(x,y,z) and N(x,y,z), the convolution product in actual space is obtained by simple multiplication of the Fourier transforms, so that the following transformation results:

$$G(x,y,z) = F(x,y,z) \cdot H(x,y,z) + N(x,y,z)$$

Furthermore, assuming that N(x,y,z) is sufficiently small, then this equation can be further approximated as follows:

$$F(x,y,z) \approx G(x,y,z)/H(x,y,z)$$

Furthermore, by applying a Fourier reverse transform to F(x,y,z), it is possible to remove blurring from f(x,y,z), i.e., from the X-ray three-dimensional image of the object of imaging, so that clearer reproduction is possible. This method is a means of image analysis that is generally referred to as the inverse filter method. In addition, there is also a Wiener inverse filter method which is an improvement of this method. It goes without saying that similar results are obtained if such a means is used.

Here, furthermore, a mathematical correction is applied after the X-ray three-dimensional image has been tentatively calculated. In some cases, however, it would also be possible to apply this correction directly to the original image. More specifically, in the case of an original image, it would also be possible to recalculate the X-ray three-dimensional image after applying a correction to I(x,y,z). This difference depends on whether the mathematical correction is applied before or after the application of the Radon theorem.

Figure 3:
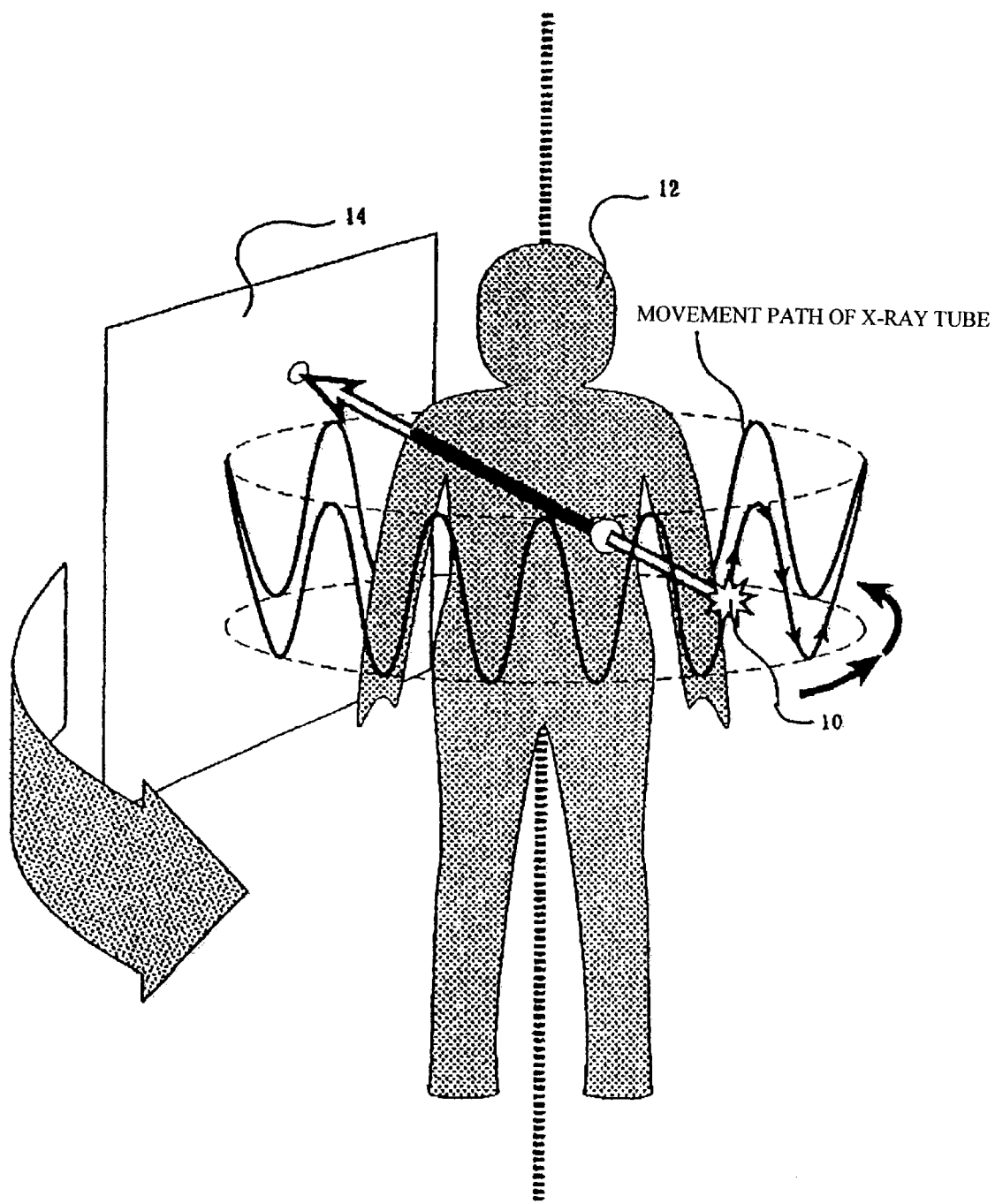
FIG. 3 is an explanatory diagram of three-dimensional imaging illustrating one example of the present invention.

Concerning the Moving Mode of the X-ray Tube and Installation of the X-ray Detector Surface An X-ray three-dimensional image of the object of imaging 12 can be obtained using the above-described means. Here, we will discuss the moving mode of the X-ray tube 10 and the installation of the X-ray detector 14. FIG. 3 shows a system of the type in which the X-ray tube 10 performs a circuit around the object of imaging (human body) 12. However, this system differs from an ordinary X-ray CT apparatus. In other words, since the X-ray detector 14 is planar, and X-ray three-dimensional image can be obtained as a result of the movement of the X-ray tube 10 around the human body, but this system differs from a conventional X-ray CT apparatus in that an X-ray three-dimensional image can be constructed even when the X-ray tube 10 performs a partial circuit that is less than half the circumference of the human body.

The configuration of the X-ray detector 14 in the present example is planar, and this detector moves in linkage with the X-ray tube 10 so that the detector is always positioned exactly opposite the X-ray tube 10 with respect to the object of imaging 12. In order to simplify this movement mechanism, it would also be possible to use a structure in which the X-ray detector 14 is formed as a tubular detector, and the X-ray tube 10 moves over the inner circumference of this detector. In FIG. 3, it is desirable that the object of imaging 12 be irradiated with X-rays from as many different directions as possible in order to obtain a clear three-dimensional image. Accordingly, in regard to the path of the X-ray tube 10, it is desirable to devise this X-ray tube 10 so that it can not only move in a circle around the object of imaging 12, but also move upward and downward. This is a movement path that could not be realized in conventional X-ray CT devices. As a result of such a device, the quality of the X-ray three-dimensional image can be improved. In the present invention, this is possible because the X-ray transmission coefficients in various parts of the object of imaging are independently measured. This is also one of the characterizing features of the present invention.

Figure 4:
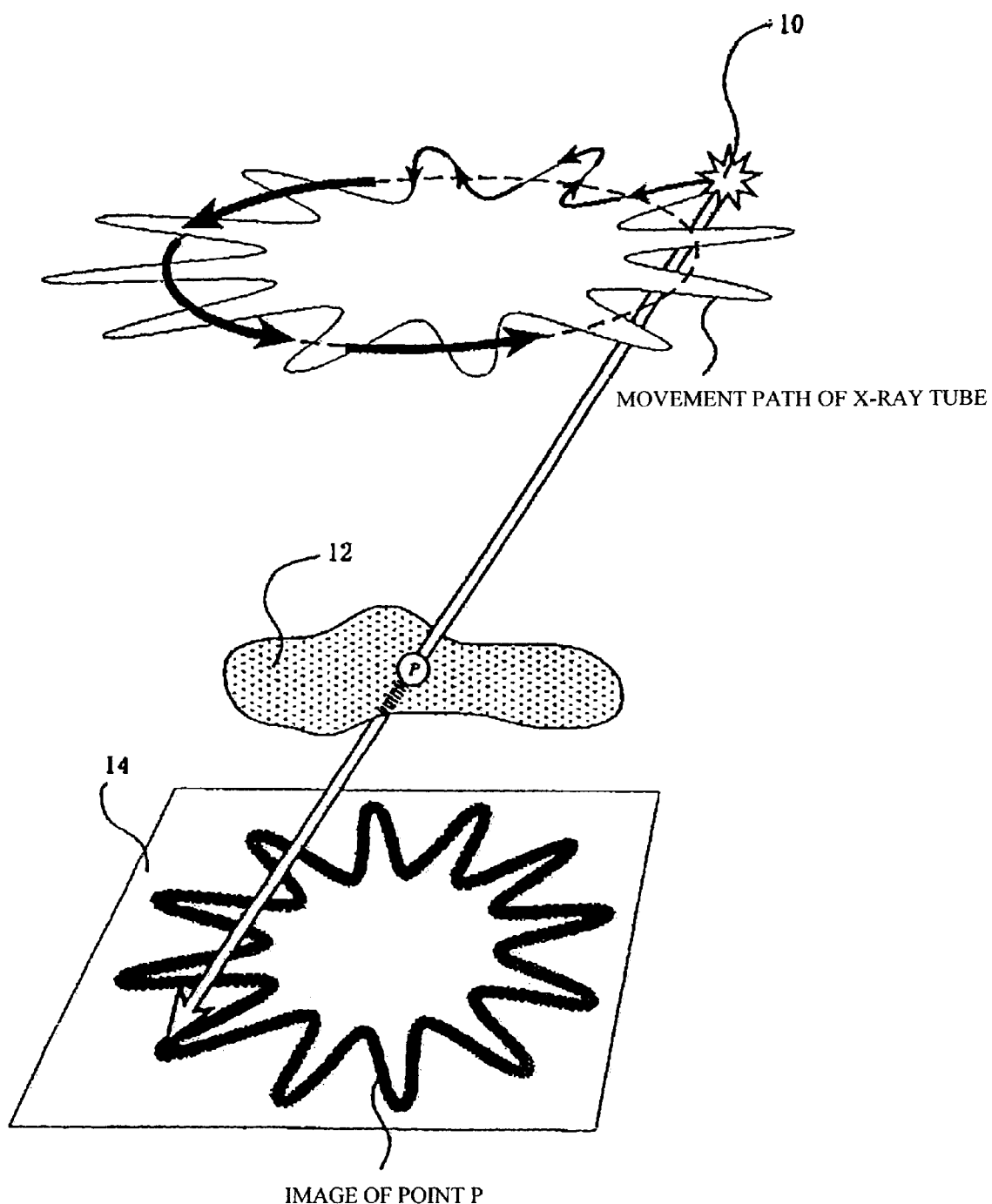
FIG. 4 is an explanatory diagram of three-dimensional imaging illustrating one example of the present invention.
Figure 7:
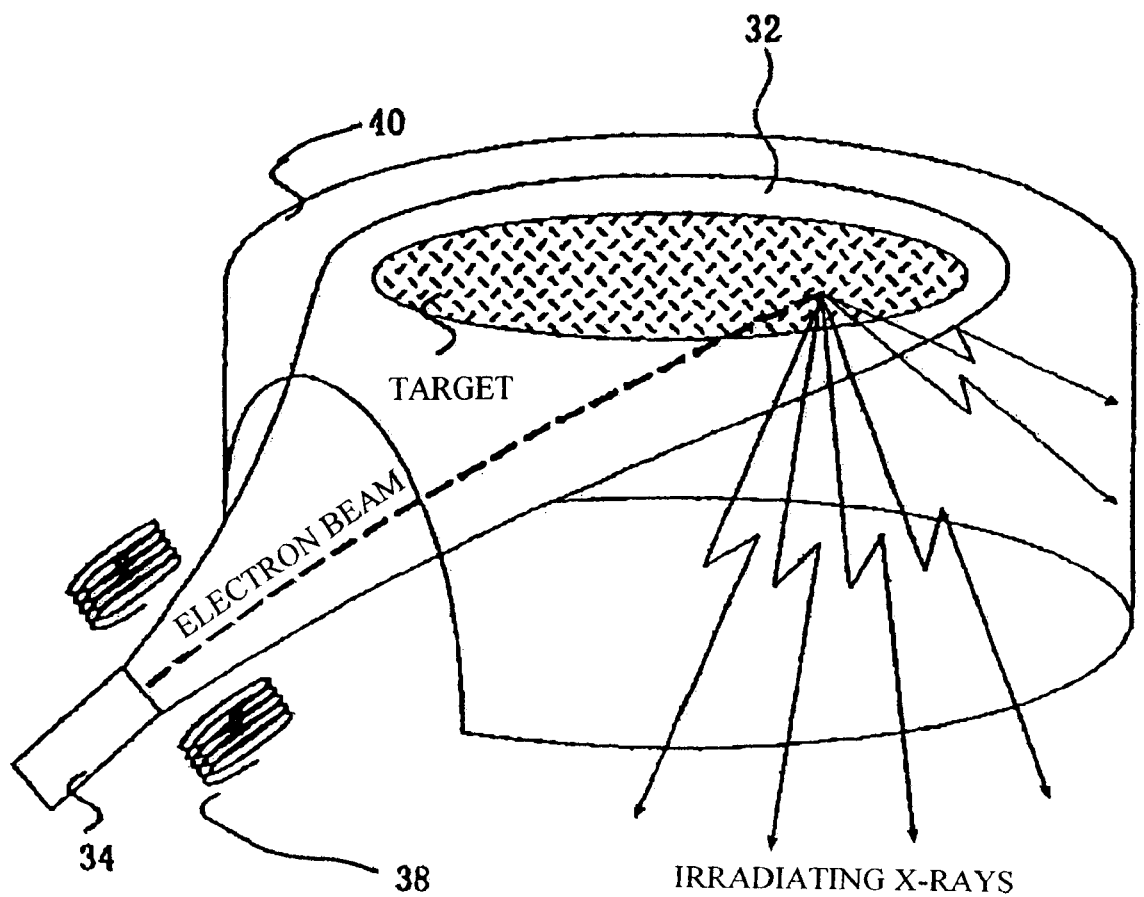
FIG. 7 is an explanatory diagram of an X-ray tube illustrating one example of the present invention.

Thus, in regard to the movement mode by which the X-ray tube 10 makes a circuit around the object of imaging 12, the X-ray detector 14 is fixed and only the X-ray tube 10 moves in FIG. 4. In the case of this movement mode, it is not necessary for the X-ray tube 10 to make a circuit around the object of imaging 12. Accordingly, an X-ray three-dimensional image can be obtained with the patient in a standing position, as though the patient were receiving a simple chest X-ray. Accordingly, since there is no need to insure a space for the movement of the X-ray tube 10 as in a conventional X-ray CT device, and no need for a mechanism that transports the patient through the device in a prone positions, the installation area required for the apparatus can be greatly reduced. Furthermore, if an electromagnetically controlled X-ray tube such as that shown in FIG. 7 is used as the X-ray tube 10, there is no need for energy to cause the physical movement of the X-ray tube 10. Accordingly, power consumption can also be greatly reduced. Furthermore, by mounting the imaging apparatus in a vehicle and making rounds in areas where medical facilities are insufficient, it is possible to offer a high degree of medical care.

Figure 5:
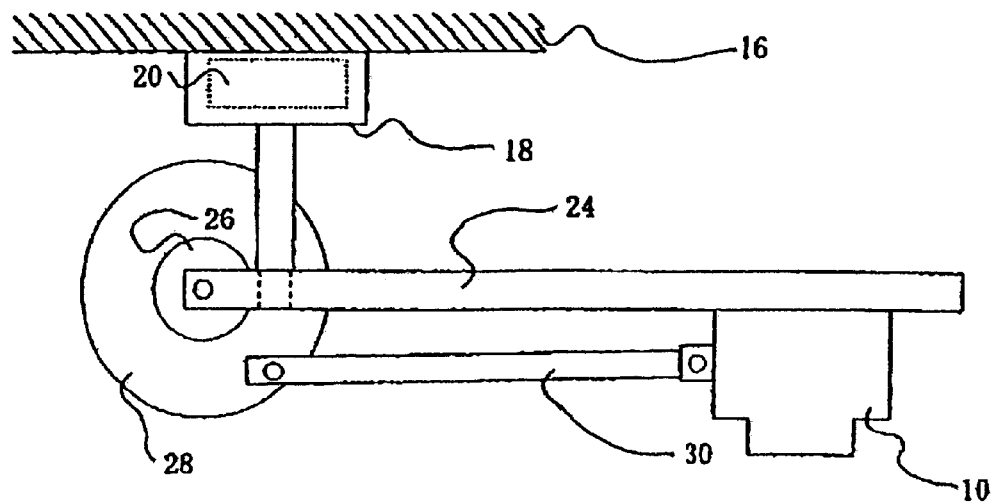
FIG. 5 is an explanatory diagram showing the movement mode of the X-ray tube, which illustrates one example of the present invention.
Figure 6:
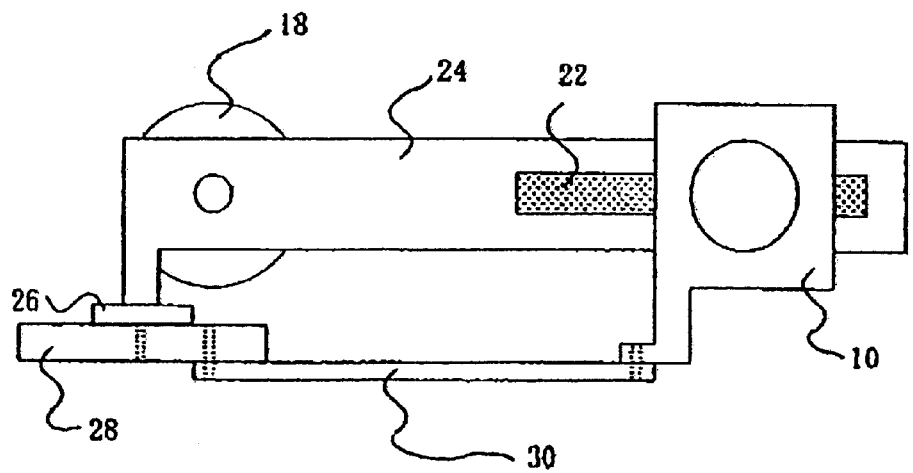
FIG. 6 is an explanatory diagram showing the movement mode of the X-ray tube, which illustrates one example of the present invention.

Here, the X-ray tube 10 generally performs a circular motion within a plane parallel to the X-ray detector 14. However, higher-precision imaging can be accomplished if the system is devised so that the radius of this circular motion can be expanded and contracted. Such an operation can be realized using an apparatus of the type shown in FIGS. 5 and 6. More specifically, a motor 20 is contained in a supporting base 18 which is attached to a fixed member 16, and a crank 24, one end of which is guided by a groove 22, and which supports an X-ray tube 10 that is capable of a reciprocating motion, is attached to this supporting base 18. Meanwhile, a disk (cam) 28 which is caused to rotate by a motor 26 is attached to the other end of the crank 24, and an eccentric position on the cam 28 is connected to the X-ray tube 10 by a cam shaft 30. As a result, when the motor 20 is caused to rotate, the crank 24 performs a reciprocating motion so that the radius of rotation expands and contracts, thus causing the X-ray tube 10 to follow a flower-petal form path of the type shown in FIG. 4.

Although the manufacture of an X-ray tube of the above-described type is easy, there are technical limits to the high-speed rotational movement that can be achieved in the case of such an X-ray tube. Accordingly, an example of an equivalent device will be shown. FIG. 7 is a model diagram of an apparatus in which the position of X-ray generation can be caused to move at an extremely high speed. An electron gun 34 is installed inside a vacuum tube 32, and an appropriately accelerated electron beam is emitted from this electron gun 34. A disk-form target 36 is located in the direction of irradiation of the electron beam. Deflection coils 38 are installed between the electron gun 34 and the target 36, and the electron beam is subjected to a Lorenz force by the magnetic fields emitted by these deflection coils 38, so that the electron beam can reach any desired position on the target 36. In the target 36, X-rays are generated at the location reached by the electron beam, and these X-rays are emitted in all directions. The cover 40 blocks X-rays that are emitted in directions not required for imaging.

If an X-ray tube with such a mechanism is used, the X-ray irradiation position can be quickly moved to any desired extent. Accordingly, high-speed scanning that could not be achieved using a conventional X-ray CT becomes possible. Consequently, even in the case of organs that perform involuntary movements such as the heart, a plurality of X-ray three-dimensional images can be obtained as a movie image by performing a plurality of scans over time.

Designing of X-ray Detector

Figure 8:
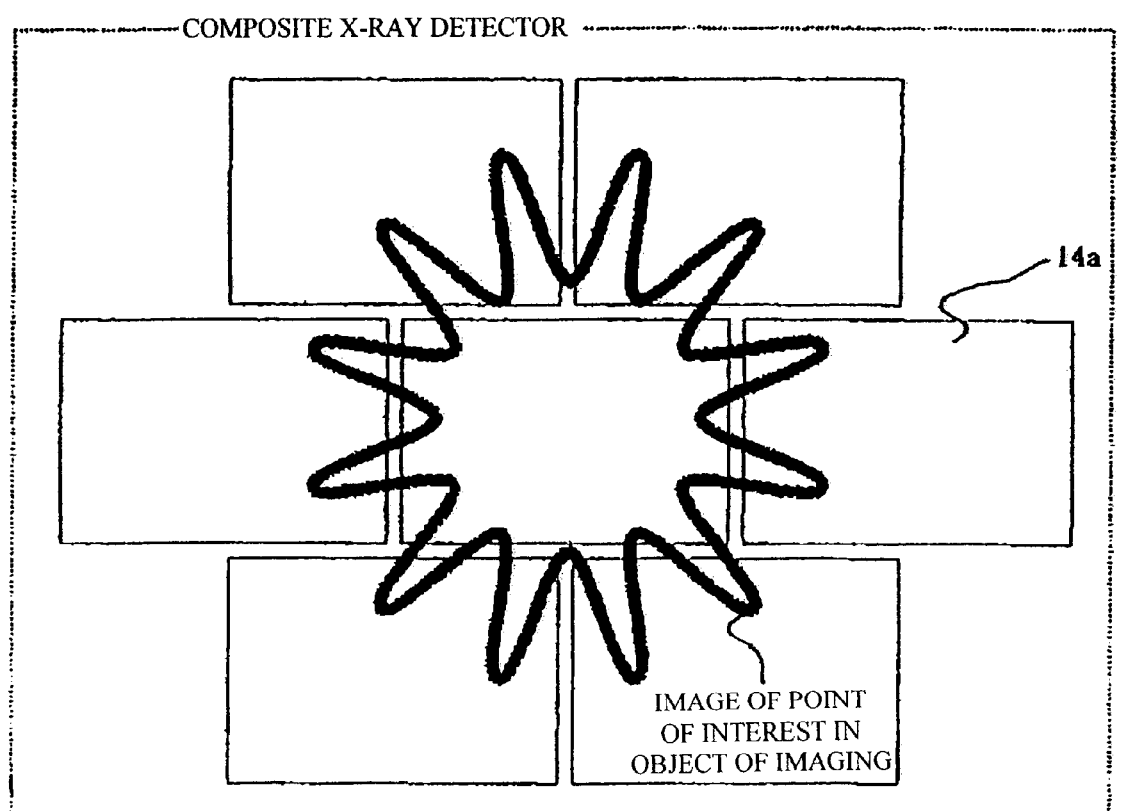
FIG. 8 is an explanatory diagram showing the aggregate state of the X-ray detector, which illustrates one example of the present invention.

In the detection surface of the X-ray detector 14, a larger surface area allows the imaging of a broader portion of the object of imaging 12. However, there may be cases in which the construction of a very large detector surface using a single detector involves technical difficulties. Accordingly, a method is conceivable in which a single large composite X-ray detection surface is constructed by forming an aggregate consisting of numerous relatively small X-ray detectors 14a as shown in FIG. 8. If the required information is positioned exactly at a joint between small detectors 14a, this information can be mathematically inferred from the information of the small detectors 14a on both sides of the joint.

Figure 9:
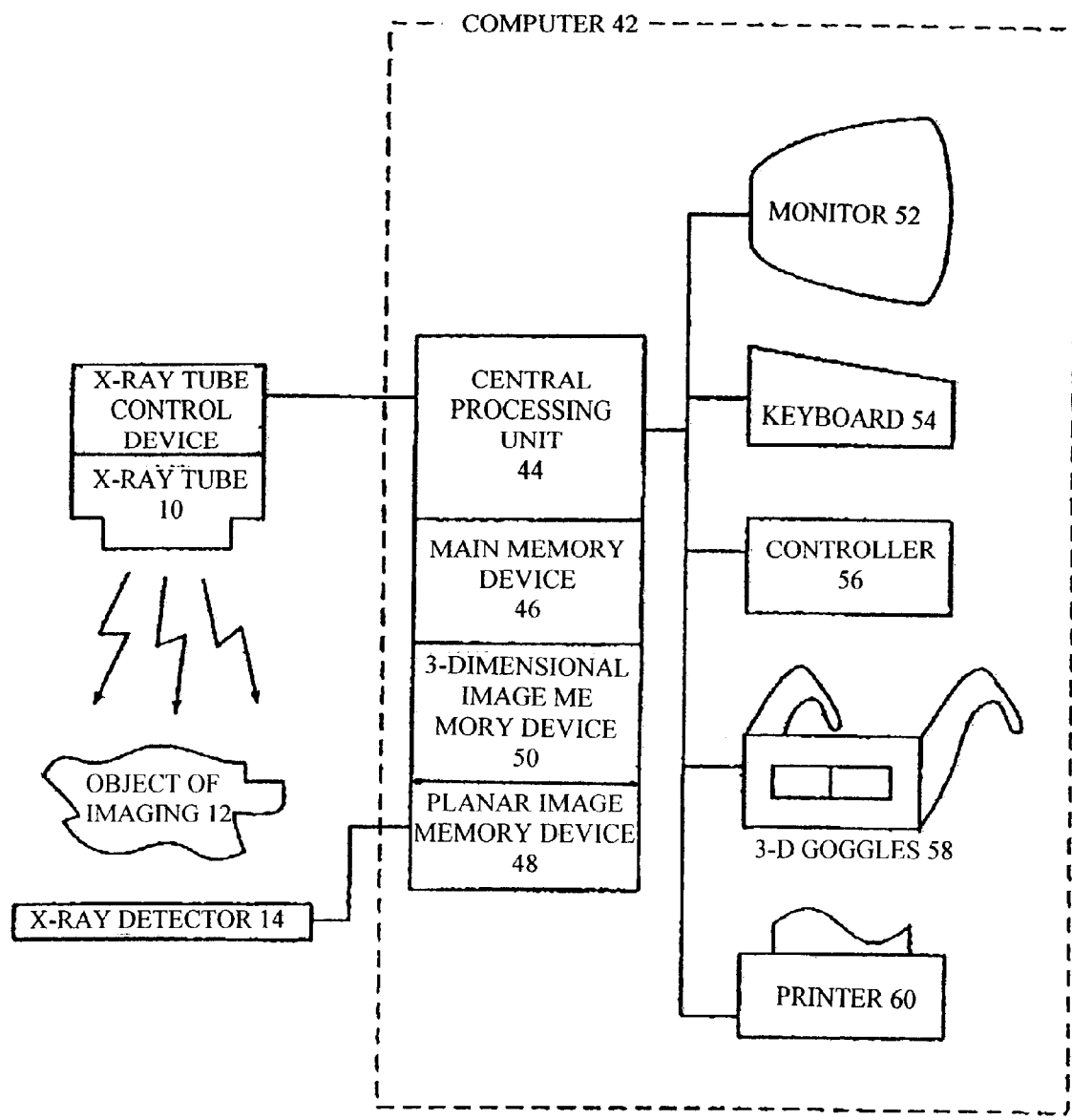
FIG. 9 is a block diagram of instruments making up a three-dimensional imaging device which illustrates one example of the present invention.
Figure 10A:
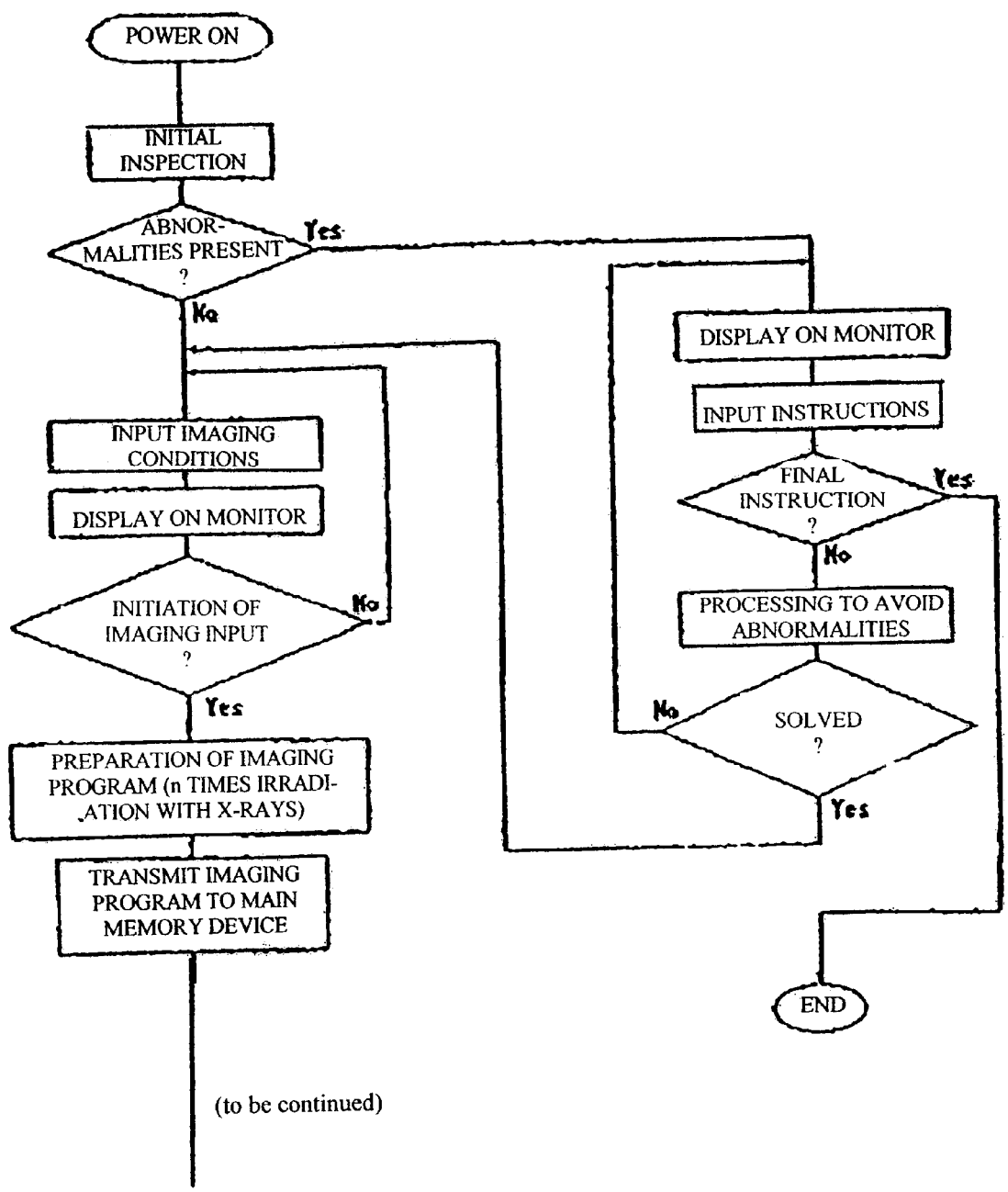
FIG. 10 (comprising 10A and 10B) is a flow chart of the operating procedure, which illustrates one example of the present invention.
Figure 10B:
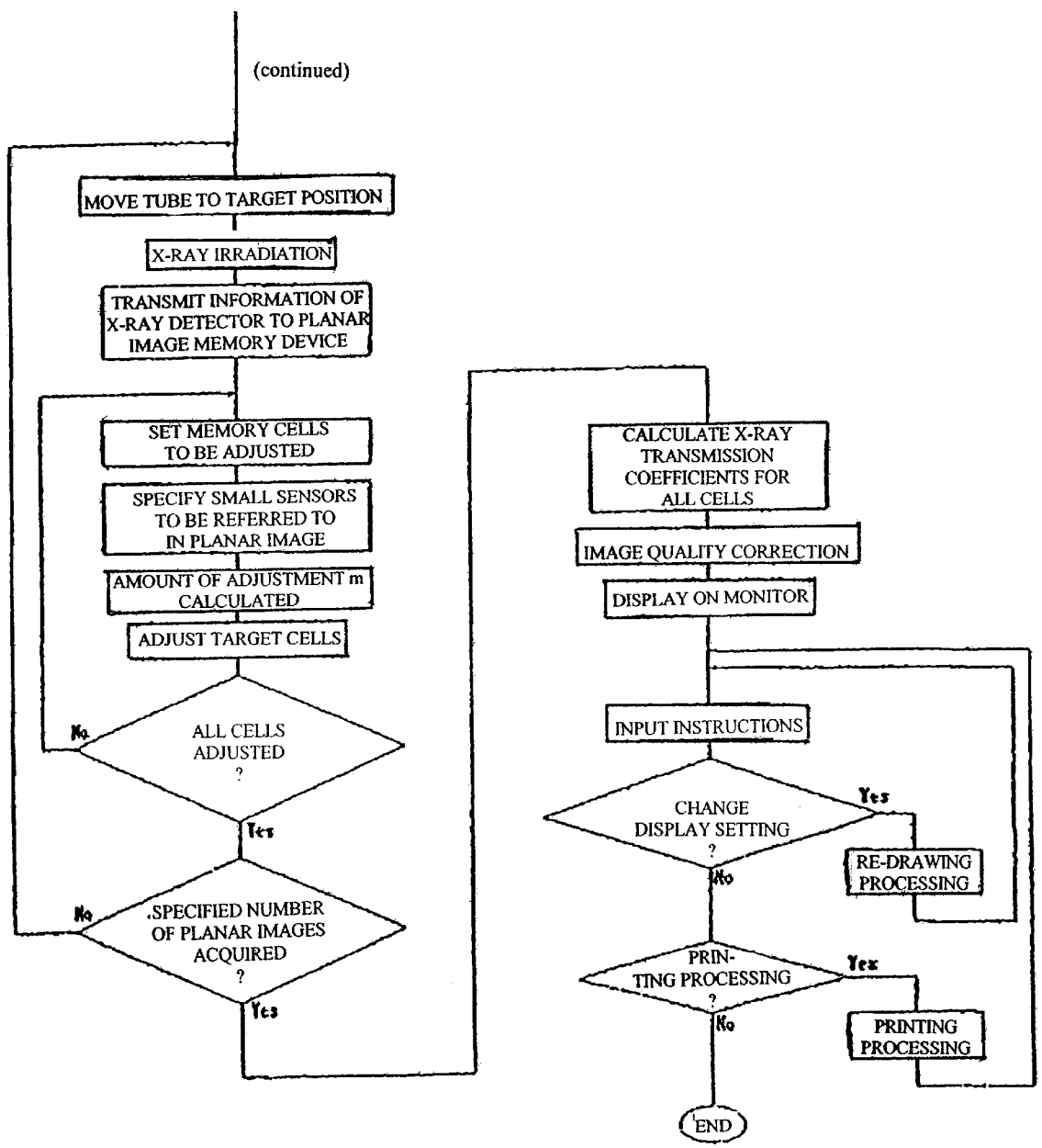
Figure 11:
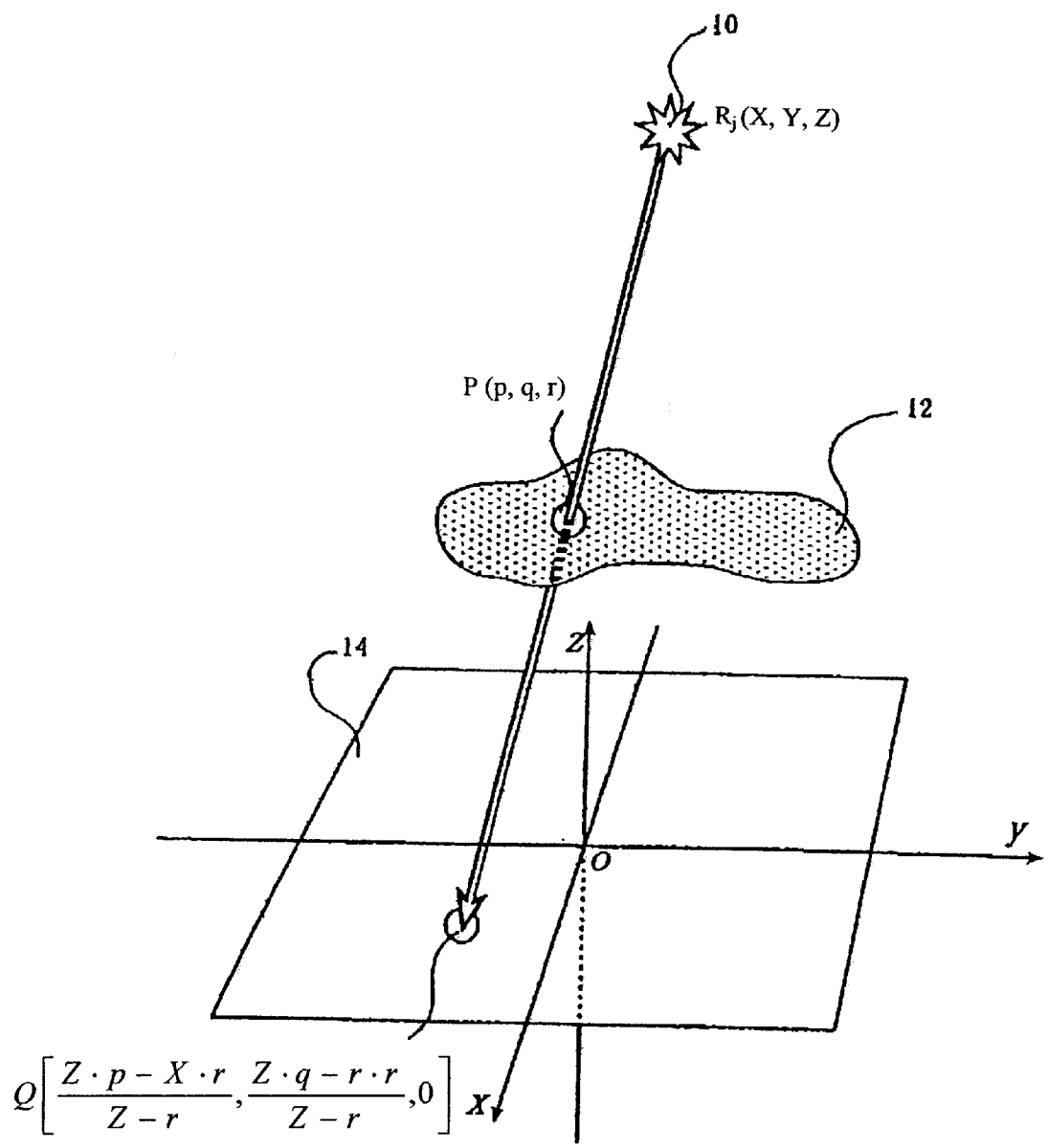
FIG. 11 is an explanatory diagram of three-dimensional imaging which illustrates one example of the present invention.

Next, a case in which the imaging of an X-ray three-dimensional image is actually performed by the above method will be described. Here, a case will be described in which the X-ray detector 14 is fixed and the X-ray tube 10 moves within a plane parallel to the X-ray detector 14 as shown in FIG. 4. However, the same effect can also be realized in a system of the type shown in FIG. 3. Accordingly, a description is omitted here. FIG. 9 is a block diagram of the present embodiment, and FIG. 10 is a flow chart of the same. Furthermore, FIG. 11 shows the positional relationship of the X-ray detector 14, object of imaging 12 and X-ray tube 10 in a three-dimensional coordinate system.

First, the instrument construction of the imaging apparatus will be outlined. The computer 42 that controls the overall apparatus is equipped with a central processing unit 44 which controls the behavior of the X-ray tube 10 and processes data from the X-ray detector 14, a main memory device 46 which stores imaging programs, an original image memory device 48 which will be described later, and a three-dimensional image memory device 50 which stores three-dimensional images, etc. In addition, the system is also equipped with a monitor 52 such as a CRT, etc., a keyboard 54, a controller 56, 3-D goggles 58 and a printer 60, etc., as input-output devices that send commands to the central processing unit 44 and receive results from the central processing unit 44.

Next, the process by which an X-ray three-dimensional image is obtained for the object of imaging 12 will be described with reference to the above-described devices, etc. When the power supply of the apparatus is switched on, the central processing unit 44 automatically checks for the presence or absence of abnormalities in the respective devices, and reports to the imaging operator via the monitor 52. Furthermore, the initialization of the main memory device 46, original image memory device 48 and three-dimensional image memory device 50, etc., is also performed at this point in time. If some abnormality should occur, the imaging operator solves the problem and indicates that the work should continue via the controller 56. The above operation is repeated until the respective devices are functioning normally.

Meanwhile, the imaging operator indicates the desired imaging conditions to the central processing unit 44 using the keyboard 54 and controller 56. The content of these instructions can be confirmed in real time via the monitor 52. In this case, the principal content of the instructions concerns the track of the X-ray tube 10, the locations to be irradiated and the radiation dosage, etc. Afterward, the imaging operator instructs the central processing unit 44 to initiate imaging via the controller 56. As a result, the central processing unit 44 initiates imaging and at the same time instantly calculates the track of the X-ray tube 10, the positions and number of times of irradiation, the dosage of the irradiating X-rays, and the timing at which the images are to be recorded, etc., on the basis of information concerning the measurement conditions. These values are recorded in the main memory device 46 as an imaging program.

Afterward, the central processing unit 44 moves the X-ray tube 10 to a specified position ($R_j$) in accordance with the imaging program, and initiates X-ray irradiation. The X-rays emitted in a radial pattern from the X-ray tube 10 advance in a straight line through the air, and reach the X-ray detector 14 after being attenuated by the object of imaging 12 positioned between the X-ray tube 10 and X-ray detector 14, so that the intensity of the X-rays, i.e., the planar density of radioactivity, is measured. In this case, it goes without saying that a larger number of pixels per unit area in the X-ray detector 14 results in a higher resolution, and is therefore desirable. The data obtained by the X-ray detector 14 is temporarily stored in the original image memory device 48 as a planar image.

Next, the central processing unit 44 begins the adjustment of the three-dimensional image memory device 50. The respective memory cells M(x,y,z) of the three-dimensional image memory device 50 correspond to the coordinates of the three-dimensional space in which the object of imaging 12 is present. Here, the adjustment of a certain memory cell M(p,q,r) will be described. In this case, the point in the object of imaging that corresponds to the memory cell M(p,q,r) is designated as P (p,q,r), and the position of the X-ray tube 10 at the point in time at which this original image is obtained is designated as $R_j(X,Y,Z)$ (j=1 for the planar image that is obtained initially). In this case, the positional relationship of the X-ray detector 14, point P(p,q.r) and point $R_j(X,Y,Z)$ is as shown in FIG. 11. Accordingly, the coordinates of point Q which is the location of the projected image of point P(p,q,r) on the X-ray detector 14 can be calculated as follows:

$$Q\left[\frac{Z\cdot p - X\cdot r}{Z-r}, \frac{Z\cdot q - r\cdot r}{Z-r}, 0\right]$$

Consequently, the planar density of radioactivity I at this point Q is obtained with reference to the pixel of the original image that corresponds to this point Q.

In the case of radially emitted X-rays, the planar density of radioactivity of the X-rays attenuates in inverse proportion to the square of the distance from the radiation source. Accordingly, a slight correction is also required for this I. In other words, the distance L between point $R_j$ and point Q at this point in time can be calculated as follows:

$$L = \left[\left[\frac{Z\cdot p - X\cdot r}{Z-r} - X\right]^2 + \left[\frac{Z\cdot q - r\cdot r}{Z-r}\right]^2 + Z^2\right]^{1/2}$$

Accordingly, I' is corrected as follows:

$$I' = L^2 \cdot I$$

Furthermore, if the planar density of radioactivity when the distance between the X-ray tube 10 and X-ray detector 14 is the unit distance is designated as I0 and the amount of adjustment of the memory cell is designated as m, then the following calculation is made:

$$m = \ln I'$$

This is added to M(p,q,r). Each time one original image is obtained, this operation is performed for all of the memory cells.

Each time that an original image is thus acquired, the operation of adjusting the contents of the three-dimensional image memory device 50 is repeated a specified number of times (n times). The greater this number of repetitions n, the higher the resolution of the X-ray three-dimensional image that is obtained. However, since the dosage received by the object of imaging is increased at the same time, this must be kept to an appropriate number of times. Furthermore, after n original images have been processed, the X-ray transmission coefficients g(x,y,z) are determined as follows from the contents of the respective memory cells:

$$g(x,y,z)=\exp[1/n\cdot M(x,y,z)-\ln I_0]$$

Then, the distribution of all of the X-ray transmission coefficients g(x,y,z) in this three-dimensional space is determined. Here, g(x,y,z) shows an X-ray three-dimensional image. However, an even clearer image can be corrected by performing an image quality correction as follows: G(x,y,z) is determined by subjecting g(x,y,z) to a three-dimensional Fourier transform as described above, and F(x,y,z) is calculated by dividing the above-described G(x,y,z) by H(x,y,z), which is the three-dimensional Fourier transform of the point image distribution function h(x,y,z) in this observation system. Then, a clearer image f(x,y,z), i.e., an X-ray three-dimensional image of the object of imaging, from which blurred images have been removed, is obtained by subjecting this to a Fourier reverse transform. Furthermore, this operation is based on an inverse filter. However, it goes without saying that mathematical processing such as a Wiener inverse filter, etc. is similarly effective, as described above.

A three-dimensional image of the object of imaging 12 is obtained in this way. In this case, however, if the imaging speed is further increased by using an X-ray tube 10 of the type shown in FIG. 7, then images that appear as though they were still images can be obtained by instantaneous imaging even in the case of organs that move involuntarily, such as the heart. Furthermore, if such imaging is performed several tens of times per second, then the beating of the patient's heart can be observed three-dimensionally in real time by successively outputting to the monitor perspective views observed from arbitrary directions.

The following means are used to observe the three-dimensional image thus obtained: The observer can give instructions by means of the controller 56 to rotate the three-dimensional image by any desired angle relative to the respective coordinate axes; and then, in each case, the central processing unit 44 calculates the view as observed from the angle indicated for the three-dimensional image, and the results are shown in real time by the monitor 52 as a perspective view.

Figure 12:
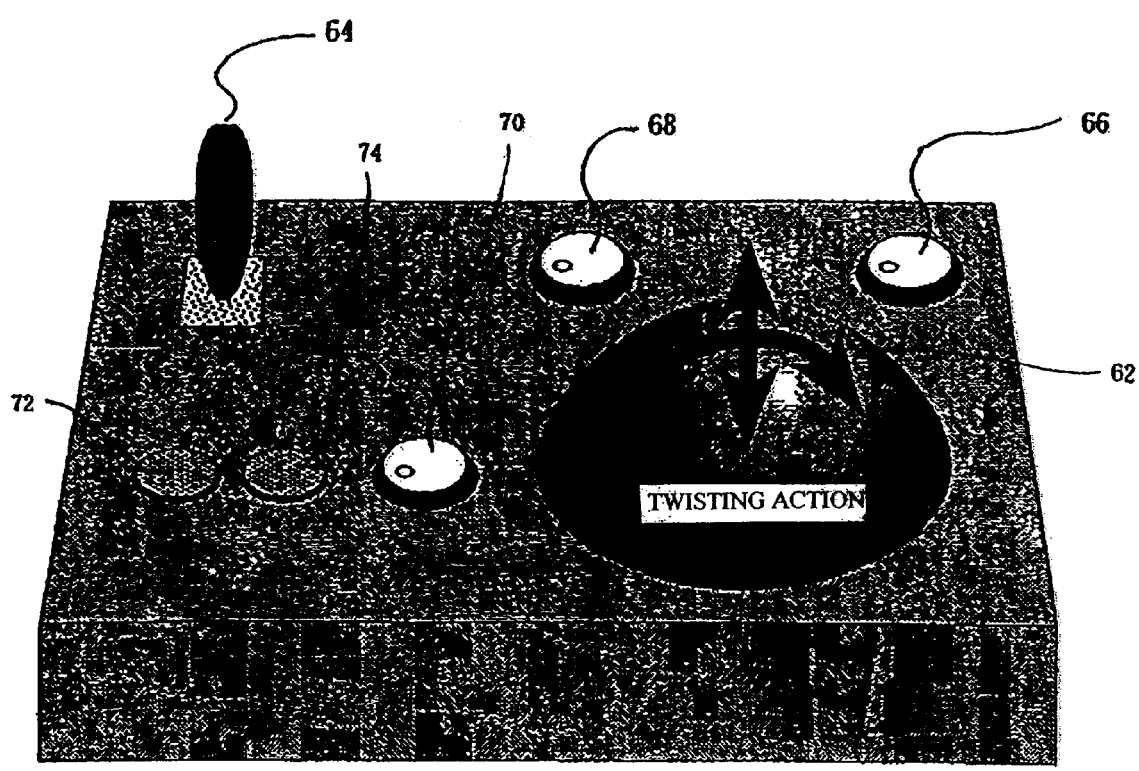
FIG. 12 is an explanatory diagram of the controller (control panel), which illustrates the principle of the present invention.

The controller 56 is equipped with a tracking ball 62 as shown in FIG. 12. However, this tracking ball 62 differs from an ordinary tracking ball in that it can be used to command a twisting action so that operating characteristics resembling rotation of the acquired three-dimensional image by hand are obtained. In addition, the controller 56 is also equipped with a joy stick 64 which performs trimming of the image in the vertical and left-right directions, an enlargement-reduction dial 68 which enlarges or reduces the image, a data entry dial 70, a decision button 72 and a cancel button 74, etc.

Furthermore, the aforementioned tracking ball 62 also has a sectional mode function which sets specified sectional planes. In concrete terms, the normal vector of the sectional plane is controlled by the rotation of the tracking ball 62 in the vertical and left-right directions, and parallel movement of the sectional plane is accomplished by twisting rotation. Accordingly, in the sectional mode, sectional planes can be observed in real time. Furthermore, in cases where a perspective view is prepared and observed, if images for the right eye and left eye are separately displayed on the monitor 52, and eyeglass type monitors (3-D goggles) 58 which can utilize this visual difference to express a three-dimensional feeling are used, the sensation of actually being present can be enhanced. In recent years, furthermore, the development of monitors that allow three-dimensional vision by the naked eye without mounting such a device on the head has been proceeding, and the use of such monitors may be expected.

Figure 13:
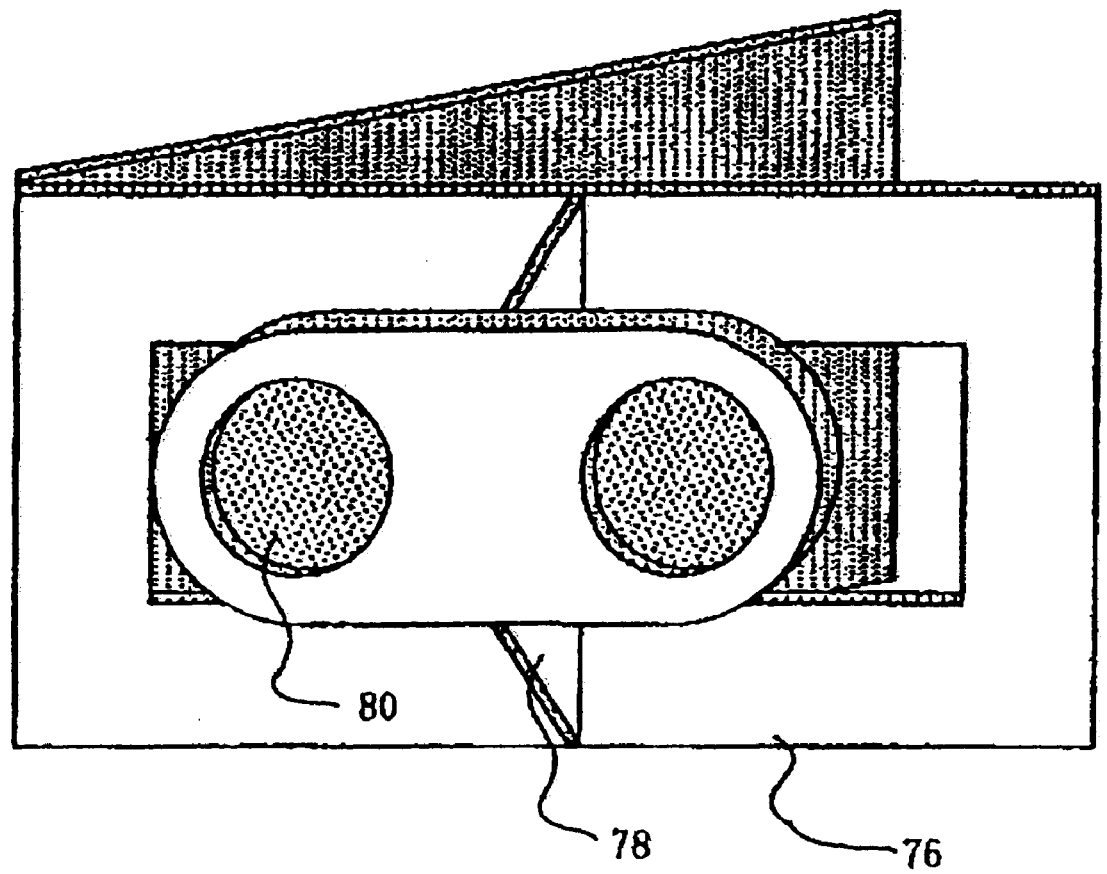
FIG. 13 is an explanatory diagram of a three-dimensional viewing instrument for acquired images, which illustrates the principle of the present invention.

Furthermore, in cases where printing is to be performed, the observer indicates this to the central processing unit 44 via the controller 56. The central processing unit 44 prepares an X-ray perspective view or sectional images of specified sectional planes under specified conditions, and outputs these images to a printer 60. Ordinary output is also possible in this case. However, if especially designated, right eye images and left eye images can be printed side by side, and this print-out can easily be viewed three-dimensionally using a device 76 of the type shown in FIG. 13. This is an instrument which has a partition plate 78 in the center in order to allow viewing of the right eye image by the right eye and the left eye image by the left eye, and which is equipped with ocular lenses 80 in order to facilitate focusing. In addition, an application in which images are printed on hologram sheets so that three-dimensional viewing by the naked eye is possible is also conceivable.

Thus, in the present invention, the X-ray transmissivity at all points in an object of imaging that has a three-dimensional extension can be investigated, i.e., an X-ray three-dimensional image can be obtained. Accordingly, the condition of the object of imaging can be grasped in greater detail, and a great effect can be obtained in the diagnosis and treatment of diseases, etc., if this invention is used in the medical field. In such cases, furthermore, X-ray three-dimensional images can be obtained in approximately the same imaging time as in ordinary X-ray CT. Accordingly, the exposure of the patient to X-rays can be reduced, and the burden on the patient (such as fixing of the body in place, etc.) can be lightened. In addition, if the imaging speed is increased, the condition of organs that constantly perform involuntary movements can also be observed.

What is claimed is:

1. An X-ray three-dimensional imaging method comprising:

the first step of irradiating an object of imaging with X-rays from an X-ray tube, detecting a planar density of radioactivity of X-rays passing through said object of imaging by an X-ray detector in which very small pixels are arranged in a planar configuration, and obtaining such radioactivity density as an X-ray original image, said first step being performed with at least positions of X-ray irradiation changed but with the X-ray tube moving in a plane parallel to the X-ray detector, thus obtaining X-ray original images at respective X-ray irradiation positions;

the second step of performing irradiation from an X-ray irradiation position in a specified position with respect to a certain observation point in said object of imaging, so that an X-ray transmissivity obtained by dividing planar density of radioactivity of X-rays passing through the observation point by planar density of radioactivity in a case where it is assumed that no object of imaging is present is obtained from pixels determined from positions of an irradiation position and observation point within said X-ray original image corresponding to said irradiation position;

the third step of determining a transmissivity of X-rays passing through said observation point by performing said second step from all other X-ray irradiation positions, so that an X-ray transmission coefficient at said observation point is obtained by subjecting transmissivity values to an averaging treatment; and the fourth step of performing said second and third steps for all observation points in said object of imaging so that X-ray transmission coefficients at respective observation points are determined, and distribution of X-ray transmission coefficients in said object of imaging is obtained as an X-ray three-dimensional image.

2. The X-ray three-dimensional imaging method according to claim 1, wherein said change of X-ray irradiation positions is accomplished by moving said X-ray tube, altering a direction of irradiation with said X-ray tube left "as is", or collecting a plurality of X-ray tubes and causing irradiation from one of said X-ray tubes.

3. The X-ray three-dimensional imaging method, wherein changes in said X-ray three-dimensional image over time are obtained as a movie image by performing said X-ray three-dimensional imaging method claimed in claim 1 or 2 a multiple number of times over a period of time.

4. The X-ray three-dimensional imaging method, wherein said X-ray three-dimensional image and X-ray original image in said X-ray three-dimensional imaging method claimed in claim 3 are subjected to a specified mathematical enhancement treatment.

5. An X-ray three-dimensional imaging apparatus comprising at least:

an X-ray tube which is capable of irradiating said object of imaging with X-rays and whose X-ray irradiation position and direction can be quickly changed;

an X-ray detector in which very mall pixels that can detect X-rays passing through said object of imaging and output a physical quantity that corresponds to a planar density of radioactivity of said X-rays are arranged in a planar configuration;

a central processing unit which controls an operation of an X-ray tube and an X-ray detector by perfoming said x-ray three-dimensional imaging method as claimed in claim 5 and which determines X-ray three-dimensional image by processing a detection data of said X-ray detector; and an output device which outputs a three-dimensional image determined by said central processing unit.

6. The X-ray three-dimensional imaging method, wherein said X-ray three-dimensional image and X-ray original image in said X-ray three-dimensional imaging method claimed in claim 1 or 2 are subjected to a specified mathematical enhancement treatment.

7. An X-ray three-dimensional image apparatus comprising at least:

an X-ray tube which is capable of irradiating said object of imaging with X-rays and whose X-ray irradiation position and direction can be quickly changed;

an X-ray detector in which very small pixels that can detect X-rays passing through said object of imaging and output a physical quantity that corresponds to a planar density of radioactivity of said X-rays are arranged in a planar configuration;

a central processing unit which controls an operation of an X-ray tube and an X-ray detector by performing said x-ray three-dimensional imaging method as claimed in claim 1 or 2 and which determines X-ray three-dimensional image by processing a detection data of said X-ray detector; and an output device which outputs a three-dimensional image determined by said central processing unit.

8. The X-ray three-dimensional imaging apparatus according to claim 7, wherein said object of imaging is positioned inside a region of movement path of said X-ray tube.

9. The X-ray three-dimensional imaging apparatus according to claim 8, wherein a position, orientation and shape of said X-ray detector is unchangeable according to movement of said X-ray tube.

10. The X-ray three-dimensional imaging apparatus according to claim 8, wherein said X-ray tube is equipped with a target that has a planar extension, and said X-ray irradiation position is controlled by using a deflection coil to change orientation of electron beam emitted from an electron gun so that a location where an electron beam strikes a target is changed.

11. The X-ray three-dimensional imaging apparatus according to claim 9, wherein said X-ray tube is equipped with a planar disk shaped target, and said X-ray irradiation position is controlled by using a deflection coil to change orientation of electron beam emitted from an electron gun so that a location where an electron beam strikes a target is changed.

12. The X-ray three-dimensional imaging apparatus according to claim 7, wherein said object of imaging is positioned outside a region of movement path of said X-ray tube.

13. The X-ray three-dimensional imaging apparatus according to claim 12, wherein a position, orientation and shape of said X-ray detector is unchangeable according to movement of said X-ray tube.

14. The X-ray three-dimensional imaging apparatus according to claim 12, wherein said X-ray tube is equipped with a target that has a planar extension, and said X-ray irradiation position is controlled by using a deflection coil to change orientation of electron beam emitted from an electron gun so that a location where an electron beam strikes a target is change.

15. The X-ray three-dimensional imaging apparatus according to claim 7, wherein a position, orientation and shape of the X-ray detector is unchangeable according to movement of the X-ray tube.

16. The X-ray three-dimensional imaging apparatus according to claim 7, wherein said X-ray tube is equipped with a planar disk shaped target, and said X-ray irradiation position is controlled by using a deflection coil to change orientation of electron beam emitted from an electron gun so that a location where an electron beam strike a target is changed.

17. The X-ray three-dimensional imaging apparatus according to claim 7, wherein a position, orientation and shape of said X-ray detector is unchangeable according to movement of said X-ray tube.

* * * * *